United States Patent [19]

Crews et al.

[11] Patent Number: 4,831,135
[45] Date of Patent: May 16, 1989

[54] BENGAMIDE ANTHELMINTICS

[75] Inventors: Philip Crews, Santa Cruz; Thomas R. Matthews, Los Gatos; Emilio Quinoa; Madeline Adamczeski, both of Santa Cruz, all of Calif.

[73] Assignees: The Regents of the University of California, Berkeley; Syntex (U.S.A.), Inc., Palo Alto, both of Calif.

[21] Appl. No.: 875,486

[22] Filed: Jun. 18, 1986

[51] Int. Cl.$^4$ .................. C07D 223/10; A61K 31/55
[52] U.S. Cl. .................... 540/526; 540/524; 540/527
[58] Field of Search .......... 540/524, 526, 527

[56] References Cited

U.S. PATENT DOCUMENTS 4,734,410 3/1988 Yanagisawa et al. .............. 514/212

FOREIGN PATENT DOCUMENTS 53-121781 10/1978 Japan ................... 540/527

Primary Examiner—Robert T. Bond
Attorney, Agent, or Firm—Irell & Manella

[57] ABSTRACT

Novel δ-caprolactam derivatives of formula I have anti-tumor, antibiotic and anthelmintic activity:

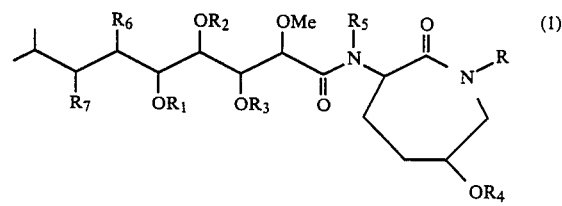

wherein:
R is H, lower alkyl, or lower acyl;
$R_1$, $R_2$, and $R_3$ are each independently H or lower acyl;
$R_4$ is H or acyl of 1 to 22 carbon atoms;
$R_5$ is H or lower acyl;
$R_6$ and $R_7$ are each H or OH, or $R_6$ and $R_7$ together form an epoxide or a double bond;
and the pharmaceutically acceptable salts thereof.

7 Claims, No Drawings

BENGAMIDE ANTHELMINTICS

REFERENCE TO GOVERNMENT GRANT

This invention was made with Government support under Grant No: NA-85-AA-D-SG140, Project #SEA-R/MP-33 with the National Oceanic and Atmospheric Administration and the University of California. The Government has certain rights in this invention.

1. Field of the Invention

This invention relates to new ε-caprolactam derivatives which have anti-tumor, antibiotic and anthelmintic activity. This invention also relates to a method for treating mammals or fowl having tumors or bacterial or parasitic infection by administering compounds of the invention, and to pharmaceutical compositions useful therefor.

2. Related Disclosure

Certain compounds of the invention, referred to herein as "bengamides," were isolated by extraction from a previously unidentified marine sponge (order Astrophorida; family Jaspidae) native to the waters surrounding the Fiji islands. These compounds, along with the other compounds of the invention, possess therapeutic activity against mammalian tumor cells, bacteria, for example *Streptococcus pyrogenes*, and against nematodes, such as *Nippostronglyus braziliensis*.

Compounds of formula 1 can be named as derivatives of ε-caprolactam. For example, where R is methyl, $R_1$–$R_3$ are all H, $R_4$ is tetradecanoyl, and $R_5$ is H, the compound is named 2-(2-methoxy-3,4,5-trihydroxy-8-methylnon-6(E)-enoylamino)-5-tetradecanoyloxy-7-methyl-ε-caprolactam.

DEFINITIONS

The term "bengamide" refers to naturally occurring compounds of formula 1:

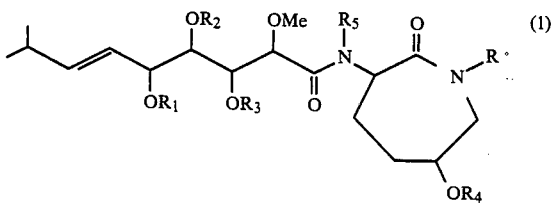

wherein:
R is H or methyl;
$R_1$, $R_2$, and $R_3$ are each H;
$R_4$ is tetradecanoyl;
$R_5$ is H; and
$R_6$ and $R_7$ together form a double bond.

"Bengamide A" refers to compounds wherein R is H, while "bengamide B" refers to compounds wherein R is methyl.

The term "pharmaceutically acceptable" as used herein includes that which is acceptable for veterinary use, and is thus not limited to suitability for human use.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, furmaric acid, tartaric acid, citric acid, benzoic acid, cinnamic acid, mandelic acid, methanesulfonic acid, ethanesulfonic acid, p-toluenesulfonic acid and the like.

The term "alkyl" as used herein refers to a straight or branched chain monovalent substituent consisting solely of carbon and hydrogen, containing no unsaturation and having from 1 to 22 carbon atoms. Examples of alkyl groups include methyl, ethyl, n-propyl, i-propyl, n-butyl, i-butyl, s-butyl and t-butyl, n-pentyl, n-hexyl, 3-methylpentyl, decyl, dodecyl, tetradecyl, eicosyl, and the like. The term "lower alkyl" refers to a straight or branched chain monovalent substituent consisting solely of carbon and hydrogen, containing no unsaturation and having from one to six carbon atoms. Examples of lower alkyl groups include methyl, ethyl, n-propyl, i-propyl, n-butyl, i-butyl, s-butyl and t-butyl, n-pentyl, n-hexyl, 3-methylpentyl, and the like.

The term "alkenyl" as used herein refers to a straight or branched chain monovalent substituent consisting solely of carbon and hydrogen, containing at least one carbon-carbon double bond, and having from 2 to 22 carbon atoms. Examples of alkenyl groups include ethenyl, propenyl, butenyl, pentenyl, hexenyl, 3-methylpentenyl, decenyl, dodecenyl, tetradecenyl, eicosenyl, and the like.

The term "acyl" as used herein refers to groups of the formula $R_aC(O)$-, where $R_a$ is alkyl or alkenyl as defined above. The term "lower acyl" as used herein refers to groups of the formula $R_bC(O)$-, where $R_b$ is lower alkyl as defined above. Thus, where $R_4$ is acyl, $R_4$ can be without limitation acetyl, propionyl, butyryl, pentanoyl, hexanoyl, 3-methylpentanoyl, decanoyl, dodecanoyl, tetradecanoyl, eicanoyl, propenoyl, 2-butenoyl, 3-butenoyl, pentenoyl, hexenoyl, 2-decenoyl, 2,4-decadienoyl, 5,7-tetradecadienoyl, and the like. Similarly, where R, $R_1$, $R_2$, $R_3$, or $R_5$ is lower acyl, one may use without limitation the radicals acetyl, propionyl, butyryl, pentanoyl, hexanoyl, 3-methylpentanoyl, propenoyl, 2-butenoyl, 3-butenoyl, pentenoyl, hexenoyl, and the like.

The term "mammal" includes all domestic and wild mammals. including without limitation cattle, horses, swine, sheep, goats, dogs, cats, rabbits deer, mink, and the like.

The term "fowl" includes all domestic and wild birds, including without limitation chickens, ducks, geese, turkeys, game hens, and the like.

The term "treatment" as used herein covers any treatment of a disease in a mammal or bird and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

SUMMARY OF THE INVENTION

One aspect of the invention is the compound of formula 1:

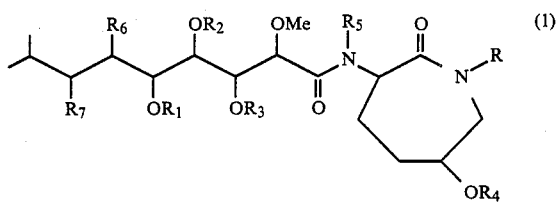

wherein:
R is H, lower alkyl, or lower acyl;
$R_1$, $R_2$, and $R_3$ are each independently H or lower acyl;
$R_4$ is H or acyl of 1 to 22 carbon atoms;
$R_5$ is H or lower acyl;
$R_6$ and $R_7$ are each H or OH, or $R_6$ and $R_7$ together form an epoxide or a double bond;
and the pharmaceutically acceptable salts thereof.

Another aspect of the invention is the method of treating a fungal infection by administering an effective amount of a compound of formula 1.

Another aspect of the invention is the method of treating a helminth infestation by administering an effective amount of a compound of formula 1.

Another aspect of the invention is a pharmaceutical composition which comprises an effective amount of a a compound of formula 1 and a pharmaceutically acceptable carrier.

Another aspect of the invention is a method for preparing a pharmaceutical agent by extracting a compound of formula 1 from a marine sponge.

DETAILED DESCRIPTION AND PRESENTLY PREFERRED EMBODIMENTS

One aspect of the invention is the compound of formula 1 and its pharmaceutically acceptable salts, particularly the compound bengamide. A presently preferred embodiment is the compound bengamide that is at least 90% pure, preferably at least 95% pure, and most preferably at least 99% pure.

Another aspect of the invention is the compound of formula 1:

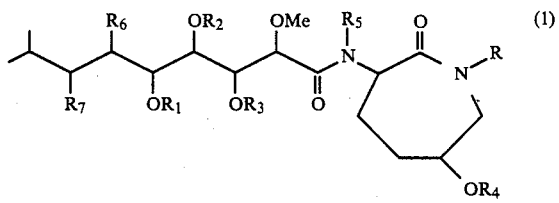

wherein:
R is H, lower alkyl, or lower acyl;
$R_1$, $R_2$, and $R_3$ are each independently H or lower acyl;
$R_4$ is H or acyl of 1 to 22 carbon atoms;
$R_5$ is H or lower acyl;
$R_6$ and $R_7$ are each H or OH, or $R_6$ and $R_7$ together form an epoxide or a double bond;
and the pharmaceutically acceptable salts thereof. A preferred class of the invention is the compound wherein $R_6$ and $R_7$ together form a double bond. A preferred subclass is the compound wherein $R_1$, $R_2$, $R_3$, and $R_5$ are each H, particularly where $R_4$ is tetradecanoyl. A presently preferred embodiment is the compound wherein R is H. Another presently preferred embodiment is the compound wherein R is methyl.

Another aspect of the invention is the method of treating a fungal infection by administering an effective amount of a compound of formula 1. A preferred class is the method which comprises administering an effective amount of a compound of formula 1 topically.

Another aspect of the invention is the method of treating a helminth infestation by administering an effective amount of a compound of formula 1. A preferred class is the method which comprises administering an effective amount of a compound of formula 1 orally.

Another aspect of the invention is the method of treating cancer by administering an effective amount of a compound of formula 1.

Another aspect of the invention is a pharmaceutical composition which comprises an effective amount of a compound of formula 1 and a pharmaceutically acceptable carrier. A preferred class is the composition which is suitable for topical application. Another preferred class is the composition which is suitable for oral administration.

PREPARATION

Bengamide can be isolated from an abundant, finger-like, orange sponge, which is previously undescribed Jaspidae sponge (order Astrophoridea; family Jaspidae) native to the waters surrounding the Fiji Islands. The sponge has the following characteristics, by which one of ordinary skill in the art may recognize the appropriate sponge and distinguish it from others:

The dermal membrane contains numerous asters 15 to 30 μm in diameter, which irregularly distributed strongyles tangential to the surface. The strongyles occur in loose bunches, some connected by spongin, and vary in measure from about 520×5 to about 680×8 to about 600×17 μm. The strongyles are often curved.

A fresh sponge is homogenized and immediately extracted with a suitable alcohol, preferably methanol, for 24 hours in a soxhlet extractor to produce a crude, viscous oil. Compounds of formula 1 form the major component in the extract, and can be detected using $^{13}C$ NMR. The alcohol extract is then successively partitioned between equal volumes of methanol (wet, % adjusted to produce a biphase solution of equal volumes) and a solvent series of: hexanes, carbon tetrachloride, and methylene chloride. The resulting $CH_2Cl_2$ and $CCl_4$ partition fractions are then purified via preparative reverse phase HPLC to yield pure bengamides. The particular compounds thus derived are 2-(2-methoxy-3,4,5-trihydroxy-8-methylnon-6(E)-enoylamino)-5-tetradecanoyloxy-7-methyl-ε-capro-lactam and 2-(2-methoxy-3,4,5-trihydroxy-8-methylnon-6(E)-enoylamino)-5-tetradecanoyloxy-ε-caprolactam.

Compounds of formula 1 may also be prepared by following the Reaction Scheme below.

REACTION SCHEME

Step 1:

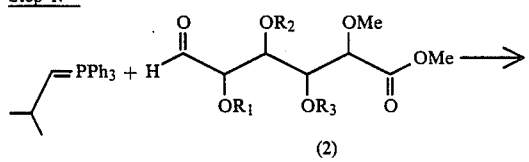

-continued
REACTION SCHEME

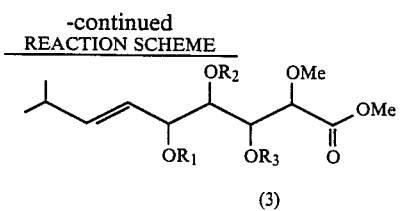

(3)

Step 2:

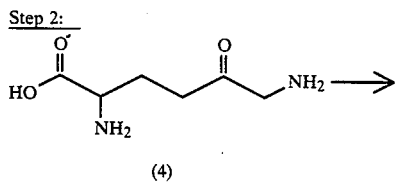

(4)

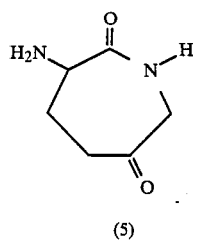

(5)

Step 3:

3 + 5 ⟶

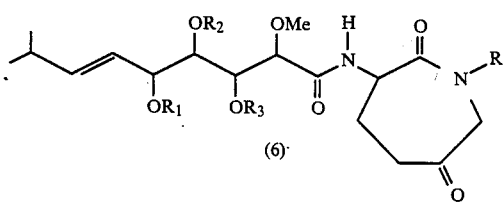

(6)

Step 4:

6 ⟶

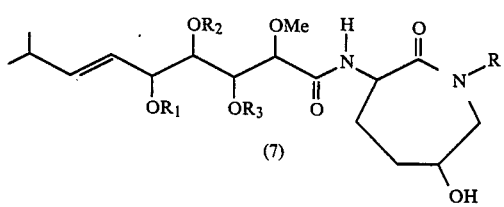

(7)

Step 5:

7 + HOR$_4$ ⟶

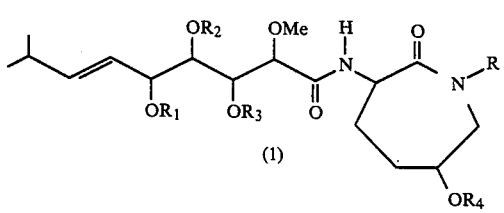

(1)

In the above Reaction Scheme, R, $R_1$, $R_2$, $R_3$, $R_4$, $R_5$, $R_6$ and $R_7$ have the same definitions as in the broadest description of the invention. Additionally, Ph denotes phenyl.

The unsaturated side chain can be prepared adding a Wittig reagent to an intermediate of formula 2 according to Step 1. Intermediates of formula 2 are esters of uronic acids, such as glucuronic acid, galacturonic acid, mannuronic acid, and the like, which are commercially available or may be prepared by one of ordinary skill in the art from any aldohexose. By judicious selection of the uronic acid, one may obtain the stereochemistry desired at $C_2$-$C_5$. For example, by reacting $(CH_3)_2CHCH=PPh_3$ with methyl 2-0-methylglucuronate under Wittig conditions, the intermediate methyl 2-methoxy-3,4,5-trihydroxy-8-methylnon-6E-enoate (3) is obtained.

The ε-caprolactam ring can be prepared by cyclizing δ-ketolysine (formula 4). This may be performed by heating the δ-ketolysine at high dilution under acid catalysis to form 4-oxo-7-amino-ε-caprolactam (formula 5). Preferably, the reaction is performed in the presence of a dehydrating agent such as dicyclohexylcarbodiimide (DCC), which is a commonly used agent for lactam and lactone preparation (Step 2).

The side chain (formula 3) and lactam (formula 5) are then condensed to form an amide of formula 6 (Step 3). For example, 4-oxo-7-amino-ε-caprolactam is heated with DCC and 2-methoxy-3,4,5-trihydroxy-8-methylnon-6E-enoic acid to provide 4-oxo-7-(2-methoxy-3,4,5-trihydroxy-8-methylnon-6E-enoylamino)-ε-caprolactam.

Next, the ketone function is reduced to an alcohol. If $R_1$, $R_2$, and $R_3$ are H, the intermediate of formula 6 is first acylated, e.g., with acetyl chloride to form the triacetate. For example, 4-oxo-7-(2-methoxy-3,4,5-trihydroxy-8-methylnon-6E-enoylamino)-ε-caprolactam is treated with acetyl chloride to produce 4-oxo-7-(2-methoxy-3,4,5-triacetoxy-8-methylnon-6E-enoylamino)-ε-caprolactam. The ketone function is then reduced under mild conditions, e.g., by treating with aluminum triisopropoxide in 2-propanol where the resulting acetone is removed by distillation (Step 4). For example, 4-oxo-7-(2-methoxy-3,4,5-triacetoxy-8-methylnon-6E-enoylamino)-ε-caprolactam is treated with aluminum triisopropoxide in 2-propanol at reflux to yield 4-hydroxy-7-(2-methoxy-3,4,5-triacetoxy-8-methylnon-6E-enoylamino)-ε-caprolactam (7).

The resulting intermediate of formula 7 may then be acylated with the appropriate acid or acyl halide (Step 5). For example, 4-hydroxy-7-(2-methoxy-3,4,5-triacetoxy-8-methylnon-6E-enoylamino)-ε-caprolactam is treated with tetradecanoyl chloride in ether to yield 4-(tetradecanoyloxy)-7-(2-methoxy-3,4,5-triacetoxy-8-methylnon-6E-enoylamino)-ε-caprolactam (1).

The resulting compounds of formula 1 may be converted to other compounds of formula 1 by techniques known to those of ordinary skill in the art. For example, 4-(tetradecanoyloxy)-7-(2-methoxy-3,4,5-triacetoxy-8-methylnon-6E-enoylamino)-ε-caprolactam may be converted to 4-(tetradecanoyloxy)-7-(2-methoxy-3,4,5-trihydroxy-8-methylnon-6E-enoylamino)-ε-caprolactam by careful saponification. Compounds of formula 1 wherein $R_6$ and $R_7$ are OH may be prepared by treating alkenes of formula 1 with $OsO_4$. Compounds of formula 1 wherein $R_6$ and $R_7$ are H may be prepared by catalytic hydrogenation of alkenes of formula 1. Compounds of formula 1 wherein $R_6$ and $R_7$ form an epoxide may be prepared by treating alkenes of formula 1 with 3-chloroperoxybenzoic acid.

Acid addition salts are prepared by reacting a free base of formula 1 with an appropriate acid. For example, bengamide is dissolved in dilute HCl to produce bengamide.HCl. Free bases of formula 1 are prepared by reacting an acid addition salt of a compound of formula 1 with an appropriate base. For example, bengamide.HCl may be treated with dilute NaOH to yield bengamide as the free base.

ADMINISTRATION AND FORMULATION

One aspect of the present invention relates to pharmaceutical and veterinary compositions useful in the treatment of tumors, fungal infection, or helmintic infection, comprising a therapeutically effective amount of a compound of formula 1, or a pharmaceutically acceptable acid addition salt thereof, in admixture with a pharmaceutically acceptable non-toxic carrier. A therapeutically effective amount is that amount which, when administered to a mammal in need thereof, is sufficient to effect treatment, as defined above.

Compounds of formula 1 are cytotoxic to tumor cells, for example larnyx epithelial carcinoma cells, at concentrations of about 1.0 µg/mL; therapeutic concentrations against other types of carcinoma may be established through in vitro tests.

Compounds of formula 1 are also effective against nematodes and other helminths, such as *Nippostrongylus braziliensis*, at concentrations of about 5 µg/mL to about 250 µg/mL.

Compounds of formula 1 are also effective antibiotics at concentrations of about 0.1 to about 100 µg/mL.

In view of the foregoing as well as in consideration of the degree of severity of the condition being treated, age of subject and so forth, all of which factors are determinable by routine experimentation by one skilled in the art, the effective dosage in accordance herewith can vary over a wide range. An "effective amount" of a compound of formula 1 for treating helminthiasis will vary depending on the species of helminth, the severity of the infection, and the animal to be treated, but may be determined routinely by one of ordinary skill in the art. In general terms, an effective amount of a compound of formula 1 for the treatment of helminthiasis will range from about 1 to about 100 mg/Kg. An "effective amount" of a compound of formula 1 for treating microbial infection will vary depending on the type and species of microbe, the severity of the infection, and the animal to be treated, but may be determined routinely by one of ordinary skill in the art. In general terms, an effective amount of a compound of formula 1 for the treatment of microbial infection will range from about 1 to about 100 mg/Kg.

Useful pharmaceutical carriers for the preparation of the pharmaceutical compositions hereof can be solids, liquids, gels, creams, ointments, and the like. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in *Remington's Pharmaceutical Sciences* by E. W. Martin.

In the practice of the above described method of the present invention a therapeutically effective amount of the compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally or intraruminally, systemically (e.g., transdermally, intranasally or by suppository), topically, or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 topically when treating fungal infestations, and orally when treating helminth infestations.

The formulation can be administered in a single unit dosage form for continuous treatment or in a single unit dosage form ad libitum when relief of symptoms is specifically required.

The compounds of formula 1 may be formulated with suitable pharmaceutical vehicles known in the art to form particularly effective topical anti-fungal compositions. An effective amount of a compound of formula 1 is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants.

Compounds of formula 1 may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before.

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those patents as is pertinent is incorporated herein by reference.

A suitable topical non-classical anhydrous, water washable "ointment type" base is described in U.S. Pat. No. 3,592,930 to Katz and Neiman, and that patent is incorporated herein by reference.

EXAMPLE 1

(Preparation of Bengamide)

Bengamide is isolated from a sponge (order Astrophorida; family Jaspidae), which is native to the waters surrounding the Fiji Islands. The sponge has the following characteristics, by which one of ordinary skill in the art may recognize the appropriate sponge and distinguish it from others:

The dermal membrane contains numerous asters 15 to 30 $\mu$m diameter, with irregularly distributed strongyles tangential to the surface. The strongyles occur in loose bunches, some connected by spongin, and vary in measure from about 520×5 to about 680×8 to about 600×17 $\mu$m. The strongyles are often curved.

The sponge is found at a depth of approximately 30 feet in Mbengga Lagoon, Fiji. It has also been found at the following Fiji Island sites:

W. Longitude—178° 09.6′, S. Latitude—18° 21.7′;
W. Longitude—177° 59.6′, S. Latitude—18° 22.7′;
W. Longitude—177° 59.2′, S. Latitude—18° 22.2′.

A fresh sponge (3 Kg wet) was homogenized and extracted with methanol (2 L) for 24 hours in a soxhlet extractor to produce a crude, viscous oil. On concentration, 7.74 g of material was obtained. Bengamides (R=H, Me) were the major component in the extract, and were detected using $^{13}$C NMR. The crude oil was then successively partitioned between equal volumes (300 mL) of MeOH (wet, % adjusted to produce a biphase solution of equal volumes) and a solvent series of hexanes, CCl$_4$, and CH$_2$Cl$_2$. The resulting CH$_2$Cl$_2$ and CCl$_4$ partition fractions were then purified via preparative reverse phase HPLC (10 $\mu$ODS column; solvent=dry CH$_3$CN) to yield pure bengamides.

EXAMPLE 2

(Characterization of Bengamide)

(A) Bengamide (R=H) displays the following characteristics:

Molecular Formula: C$_{31}$H$_{56}$O$_8$N$_2$
Optical rotation: $[\alpha]_D$= +30.3° (c=8.1×10$^{-2}$, MeOH)
m.p.=114°–115° C.
IR (neat): 3700–3100, 1740, 1660, 1650 cm$^{-1}$
NMR: (See Table 1)

(B) Bengamide (R=Me) is a viscous oil which displays the following characteristics:

Molecular Formula: C$_{32}$H$_{59}$O$_8$N$_2$
Optical rotation: $[\alpha]_D$= +34.6° (c=7.5×10$^{-2}$, MeOH)
IR (neat): 3700–3100, 1740, 1670, 1660 cm$^{-1}$
NMR: (See Table 2)

(C) Triacetyl bengamide (R=H, Me) was also prepared, and an NMR spectrum obtained (see Table 3).

TABLE 1

NMR Data Bengamide (R = H)

| Atom Number | $^1$H $\delta$, mult=J in Hz CDCl$_3$ | $^1$H $\delta$, mult=J in Hz CDCl$_3$/C$_6$D$_6$ 50% | $^{13}$C $\delta$, APT mult CDCl$_3$ |
|---|---|---|---|
| 1 | 0.99 d = 6.9, 3 H (e)* | 1.00 d = 6.9, 3 H (d) | 22.3 q |
| 2 | 2.29 m (c) | 2.28 m | 30.9 d |
| 3 | 5.78 dd = 15.5, 6.5 | 5.82 dd = 15.3, 6.6 | 141.9 d |
| 4 | 5.44 dd = 15.5, 7.3 | 5.55 dd = 15.3, 6.9 | 125.5 d |
| 5 | 4.21 t = 6 | 4.29 bs | 74.3 d |
| 6 | 3.60 bs | 3.68 bs | 72.5 d |
| 7 | 3.80 m (b) | 3.91 bs | 72.8 d |
| 8 | 3.80 m (b) | 3.80 d = 6.3 | 81.3 d |
| 9 | | | 172.3 s |
| 10 | 4.60 m (a) | 4.48 m (a) | 51.5 d |
| 11 | 2.15 m (d) 1.75 m | 1.99 m (b) 1.50 m (c) | 28.9 t |
| 12 | 2.15 m (d) 1.95 m | 1.99 m (b) 1.75 m | 33.0 t |
| 13 | 4.60 m (a) | 4.48 m (a) | 70.9 d |
| 14 | 3.32 bm, 2 H | 2.90 bm, 2 H | 45.2 t |
| 15 | 0.99 d = 6.9, 3 H (e) | 0.99 d = 6.6, 3 H (d) | 22.2 q |
| 16 | | | 173.0 s |
| 17 | | | 174.2 s |
| 18 | 2.29 t = 7.5, 2 H (c) | 2.17 t = 7.5 (2 H) | 34.4 t |
| 19 | 1.59 m 2 H | 1.57 m 2 H (c) | 25.0 t |
| 20–27 | 1.4–1.2 bs 20 H (f) | 1.4–1.2 bs, 20 H (e) | 29.7–29.2 t |
| 28 | (f) | (e) | 32.0 t |
| 29 | (f) | (e) | 22.8 t |
| 30 | 0.87 t = 6.5, 3 H | 0.93 t = 6.5, 3 H | 14.2 q |
| a | 8.10 d = 6.3 (10%) 7.97 d = 6.3 (190%) | 8.20 d = 3.6 (10%) 8.05 d = 3.6 (190%) | |
| b | 6.28 t = 6.3 | 6.08 bs | |
| OH | 4.27 bs | 4.48 m (a) | |
| OMe | 3.52 s 3 H | 3.33 s 3 H | 60.0 q |

*The letters in parentheses indicate overlapping signals.

TABLE 2

NMR Data Bengamide (R = Methyl)

| Atom Number | $^1$H $\delta$, mult = J in Hz CDCl$_3$ | $^1$H $\delta$, mult = J in Hz CD$_3$OD | $^{13}$C $\delta$, APT mult CDCl$_3$ | $^{13}$C $\delta$, APT mult CD$_3$OD |
|---|---|---|---|---|
| 1 | 0.95 d = 6.3, 3 H (e) | 0.90 d = 6.6, 3 H (e) | 22.2 q | 22.7 q |
| 2 | 2.26 m (b) | 2.22 m (b) | 30.7 d | 32.1 d |
| 3 | 5.72 dd = 15.6, 6.3 | 5.63 dd = 15.5, 6.7 | 141.6 d | 142.0 d |
| 4 | 5.40 dd = 15.6, 7.1 | 5.33 dd = 15.6, 7.5 | 125.4 d | 127.5 d |
| 5 | 4.17 t = 6 | 4.02 t = 7.2 | 74.1 d | 74.9 d |
| 6 | 3.55 bd = 5.1 | 3.75 –3.66 m (a) | 72.5 d (b) | 72.5 d |
| 7 | 3.76 bs (a) | 3.75–3.66 m (a) | 72.5 d (b) | 74.2 d |
| 8 | 3.76 bs (a) | 3.46 d = 6.9 | 81.1 d | 83.4 d |
| 9 | — | — | 171.8 s (a) | 172.9 s |
| 10 | 4.64 m | 4.68 bd = 11.7 | 51.2 d | 52.6 d |
| 11 | 2.10 m (c) 1.57 m (d) | 1.99 m (c) 1.55 m (d) | 28.9 t | 29.7 t |
| 12 | 2.10 m (c) 1.95 m | 1.99 m (c) 1.86, m | 32.6 t | 33.5 t |
| 13 | 4.55 bt | 4.52 bt | 69.1 d | 70.6 d |
| 14 | 3.63 dd = 15.0, 9.9 | 3.66 m (a) | 53.3 t | 54.0 t |
| | 3.18 bd = 15.0 | 3.18, bd = 10.2 | | |
| 15 | 0.95 d = 6.3, 3 H (e) | 0.90 d = 6.6, 3 H (e) | 22.1 q | 22.6 q |
| 16 | — | — | 171.8 s (a) | 173.9 s |

TABLE 2-continued

NMR Data
Bengamide (R = Methyl)

| Atom Number | $^1H$ δ, mult = J in Hz CDCl$_3$ | $^1H$ δ, mult = J in Hz CD$_3$OD | $^{13}C$ δ, APT mult CDCl$_3$ | $^{13}C$ δ, APT mult CD$_3$OD |
|---|---|---|---|---|
| 17 | — | — | 173.0 s | 174.3 s |
| 18 | 2.26 bt = 7.5 (b) | 2.22 bt = 7.2 (b) | 34.3 t | 35.1 t |
| 19 | 1.57 m 2 H (d) | 1.50 m 2 H (d) | 24.8 t | 25.9 t |
| 20–27 | 1.4–1.2, bs, 20 H (f) | 1.3–1.1 bs 20 H (f) | 29.7–29.2 t | 30.7–30.1 t |
| 28 | (f) | (f) | 31.9 t | 33.0 t |
| 29 | (f) | (f) | 22.6 t | 23.7 t |
| 30 | 0.83 t = 7.3, 3 H | 0.79 t = 6.9, 3 H | 14.1 q | 14.5 q |
| a | 8.04 d = 6 (190%) 7.92 d = 6 (10%) | | | |
| b | | | | |
| OH | 4.27 bs | | | |
| OMe | 3.47 s 3 H | 3.30 s 3 H | 59.7 q | 58.7 q |
| NMe | 3.05 s 3 H | 2.95 s 3 H | 36.3 q | 36.5 q |

TABLE 3

NMR Data (continuation)

| Atom Number | Compound 3* $^1H$ δ, mult = J in Hz (CDCl$_3$) | Compound 4* $^1H$ δ, mult = J in Hz (CDCl$_3$) |
|---|---|---|
| 1 | 0.94 d = 6.6, 3H (f) | 0.94 d = 6.6 (g) |
| 2 | 2.29 m (b) | 2.30 m (c) |
| 3 | 5.70 dd = 15.5, 6.5 | 5.70 dd = 15.6, 6.3 |
| 4 | 5.25 dd = 15.5, 5.1 | 5.25 dd = 15.3, 6.3 |
| 5 | 5.50 m (a) | 5.50 m (a) |
| 6 | 5.37 t = 5.0 | 5.36 t = 4.8 |
| 7 | 5.50 m (a) | 5.50 m (a) |
| 8 | 3.79 d = 6.5 | 3.76 d = 4.5 |
| 9 | — | — |
| 10 | 4.51 m | 4.58 m (b) |
| 11 | 2.15 m (c) 1.62 m (d) | 2.15 m (d) 1.60 m (f) |
| 12 | 2.15 m (c) 1.95 m (e) | 2.15 m (d) 2.00 m (e) |
| 13 | 4.61 bt | 4.58 m (b) |
| 14 | 3.26 bm, 2 H | 3.67 dd = 14.7, 10 3.19 bd = 14.7 |
| 15 | 0.94 d = 6.6, 3 H (f) | 0.94 dd = 6.6 (g) |
| 16 | — | — |
| 17 | — | — |
| 18 | 2.29 bt = 7.5, 2 H (b) | 2.30 bt = 7.5, 2 H (c) |
| 19 | 1.62 m 2 H (d) | 1.60 m 2 H (f) |
| 20–27 | 1.4–1.2 bs 20 H (g) | 1.4–1.2 bs 20 H (h) |
| 28 | (g) | (h) |
| 29 | (g) | (h) |
| 30 | 0.87 t = 6.5, 3 H | 0.87 t = 6.5, 3 H |
| a | 7.95 d = 6.3 (10%) 7.82 d = 6.3 (190%) | 7.95 d = 5.1 (190%) 7.82 d = 5.1 (10%) |
| b | 5.86 t = 6.3 | |
| OH | | |
| OMe | 3.40 s, 3 H | 3.39 s 3 H |
| NMe | | 3.09 s 3 H |
| AcO | 2.09 s, 3 H; 2.05, s, 6 H (e) | 2.08 s 3 H; 2.05, s, 6 H (e) |

*"Compound 3" refers to triacetyl bengamide (R = H), and "compound 4" refers to triacety bengamide (R = Me).

EXAMPLE 3

(Formulations)

(A) The following example illustrates the preparation of representative pharmaceutical formulations containing an active compound of formula 1:

| I.V. Formulation | |
|---|---|
| Compound of formula 1 | 1.0 mg |
| Propylene glycol | 20.0 g |
| Polyethylene glycol 400 | 20.0 g |
| Tween 80 | 1.0 g |
| 0.9% Saline solution qs | 100.0 ml |

The compound of formula 1 is dissolved in propylene glycol, polyethylene glycol 400 and Tween 80. A sufficient quantity of 0.9% saline solution is then added with stirring to provide 100 mL of the I.V. solution which is filtered through a 0.2 micron membrane filter and packaged under sterile conditions.

(B) A tablet formulation is prepared as follows:

| | Parts |
|---|---|
| Bengamide | 5.0 |
| Magnesium stearate | 0.75 |
| Starch | 0.75 |
| Lactose | 29.0 |
| PVP (polyvinlypyrolidone) | 0.75 |

The above ingredients are combined and granulated using methanol as the solvent. The formulation is then dried and formed into tablets (containing 500 mg of active compound) with an appropriate tabletting machine.

(C) A typical cream base formulation is as follows:

| | |
|---|---|
| Water/glycol mixture (15% or more glycol) | 50–99% |
| Fatty Alcohol | 1–20% |
| Non-ionic Surfactant | 0–10% |
| Mineral Oil | 0–10% |
| Adjuvants | 0–5% |
| Bengamide | 0.001–10% |

The fatty alcohol, non-ionic surfactant, and other adjuvants are discussed in U.S. Pat. No. 3,934,013 to Poulsen which is incorporated herein by reference.

(D) Following is an example of a typical "classical" ointment base:

| | |
|---|---|
| White Petrolatum | 40–94% |
| Mineral Oil | 5–20 |
| Glycol Solvent | 1–15 |
| Surfactant | 0–10 |
| Stabilizer | 0–10 |
| Bengamide | 0.001–10.0 |

(E) Following is a typical ointment base formulation containing propylene carbonate:

| | |
|---|---|
| Bengamide | 0.001–10.0% by weight |
| Propylene Carbonate | 1–10% |
| Solvent | 1–10% |
| Surfactant | 0–10% |
| White Petrolatum | 70–97% |

Suitable solvents, surfactants, stabilizers, etc. are discussed in U.S. Pat. No. 3,934,013, incorporated herein by reference.

(F) A representative composition utilizing a non-classical anhydrous, water washable ointment type base is as follows:

| | |
|---|---|
| Glycol Solvent | 40–35% by weight |
| Fatty Alcohol | 15–45% |
| Compatible Plasticizer | 0–15% |
| Coupling Agent | 0–15% |
| Penetrant | 0–20% |
| Bengamide | 0.001–10.0% |

EXAMPLE 4

(Esterification)

A mixture of bengamide (0.5 g) in methanol (100 mL) is treated with acetyl chloride (0.1 g) to prepare the acetylated bengamide derivative.

EXAMPLE 5

(Epoxidation)

A mixture of bengamide (0.5 g) in $CH_2Cl_2$ (100 mL) is treated with 3-chloroperoxybenzoic acid (0.1 g) to prepare the epoxidized bengamide derivative.

EXAMPLE 6

(6′,7′-Diol Formation)

Osmium tetroxide (4.4 mg) is slowly added to a stirred solution of bengamide (10.6 mg) in dry pyridine (2 mL) under a nitrogen atmosphere. After about 20 min., the reaction is judged by tlc. Then, a solution of $NaHSO_3$ (0.11 g in 1.7 mL $H_2O$) is added dropwise and stirred for 15 min. The solution is then extracted with $CHCl_3$ (3×6 mL). Concentration of the $CHCl_3$ extract and purification of the residue by reverse phase HPLC (10 μODS column, 25% MeOH/$H_2O$) yields bengamide-6′,7′-diol as a white powder. The $^1H$ NMR (100 MHz) spectrum in $CD_3$-OD exhibits the characteristic bengamide spectrum minus the vinyl methyl peak, with three new peaks in the alkyl range.

EXAMPLE 7

(Reduction)

A mixture of bengamide (0.5 g) in $CH_2Cl_2$ (100 mL) is treated with $LiAlH_4$ (0.1 g) to prepare the 6′,7′-dihydrobengamide derivative.

EXAMPLE 8

(Anthelmintic Activity)

A compound of formula 1 is given at 1000 ppm/test in Rodent Laboratory Chow 5001-meal for 4 days for the larval and adult stages of infection. Treatment is begun 24 h post-infection for the larval stage, and on day 12 post-infection for the adult stage. The subject animals are male Swiss Webster mice (12–14 g on arrival, 18–20 g when infected) obtainable from Simonsen, Gilroy, CA.

The helminths administered are *A. tetraptera, S. obvelata, N. dubius,* and *H. nana.*

Day 1 pre-infection the mice are weighed and randomized into groups of 4. The weight range for mice in treated groups is 18–20 g. After weighing and randomizing, the mice are allowed to ingest the food/bengamide mixture ad lib 24 hours/day for 4 days. Untreated mice eat standard rodent food pellets. Treatment groups are then administered helminth eggs or larvae at 0.2 mL/mouse p.o.

Mice are examined for drug activity against larvae at day 6 or 7 post-infection. Mice are examined for drug activity against adult stages at day 17 or 18 post-infection.

Using a dissecting scope, the different sections of intestine are examined for parasite worm burden. Each of the four different parasites is counted separately and recorded for each mouse. Then, an average of each parasite is calculated for the group. The percent reduction of each parasite as compared to the untreated controls is then calculated.

Compounds of formula 1 demonstrate anthelmintic activity in this assay.

What is claimed:

1. A compound of formula 1:

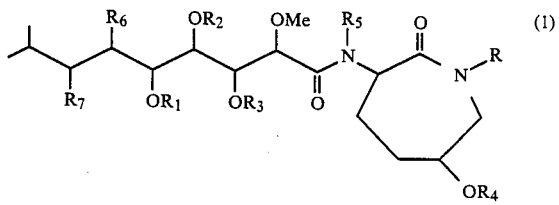

wherein:
R is H, lower alkyl, or lower alkanoyl;
$R_1$, $R_2$, and $R_3$ are each independently H or lower alkanoyl;
$R_4$ is H or alkanoyl of 1 to 22 carbon atoms;
$R_5$ is H or lower alkanoyl;
$R_6$ and $R_7$ are each H or OH, or $R_6$ and $R_7$ together form an epoxide or a double bond;
and the pharmaceutically acceptable salts thereof.

2. The compound of claim 1 wherein $R_6$ and $R_7$ together form a double bond.

3. The compound of claim 2 wherein $R_1$, $R_2$, $R_3$, and $R_5$ are each H.

4. The compound of claim 3 wherein $R_4$ is tetradecanoyl.

5. The compound of claim 4 wherein R is H or methyl.

6. The compound of claim 5 wherein R is H.

7. The compound of claim 5 wherein R is methyl.

* * * * *